United States Patent [19]

Hermecz et al.

[11] Patent Number: 4,806,645
[45] Date of Patent: Feb. 21, 1989

[54] BORIC ANHYDRIDES OF 6-FLUORO-7-CHLORO-1-METHYLAMINO-4-OXO-1,4-DIHYDRO-QUINOLINE-3-CARBOXYLIC ACID

[75] Inventors: István Hermecz; Géza Kereszturi; Lelle Vasvári; Ágnes Horv/ th, all of Budapest; M/ ria Balogh, Dunakeszi; G/ bor Kov/ cs, Budapest; Zolt/ n Mészáros, deceased, late of Budapest, by Márta Mészáros, Meszaros née Márta Bölöni, heirs; P/ ter Ritli, Budapest; Judit Sipos, Budapest; Anikó Pajor, Budapest, all of Hungary

[73] Assignee: Chinoin Gyogyszer es Vegyeszeti Termekek Gyara Rt., Budapest, Hungary

[21] Appl. No.: 105,295

[22] PCT Filed: Dec. 9, 1986

[86] PCT No.: PCT/HU86/00066
§ 371 Date: Aug. 7, 1987
§ 102(e) Date: Aug. 7, 1987

[87] PCT Pub. No.: WO87/03594
PCT Pub. Date: Jun. 18, 1987

[30] Foreign Application Priority Data

Dec. 9, 1985 [HU] Hungary ................... 4690

[51] Int. Cl.[4] ................... C07F 5/02; C07F 5/04; C07D 215/56
[52] U.S. Cl. ................... 546/13; 546/156
[58] Field of Search ................... 546/13; 514/64

[56] References Cited

U.S. PATENT DOCUMENTS 4,182,880 1/1980 Watanabe et al. ................... 546/13

OTHER PUBLICATIONS

Chemical Abstracts vol. 103(15) Abst. No. 103:123491p, Oct. 14, 1985.
Chemical Abstracts vol. 105(17), Abst. No. 153,293j, Oct. 27, 1986.

Primary Examiner—Alan L. Rotman
Attorney, Agent, or Firm—Herbert Dubno; Jonathan Myers

[57] ABSTRACT

The invention relates to new 6-fluoro-7-chloro-1-methylamino-4-oxo-1,4-dihydro-quinoline-3-carboxylic acid/boric acid anhydrides of the general Formula I

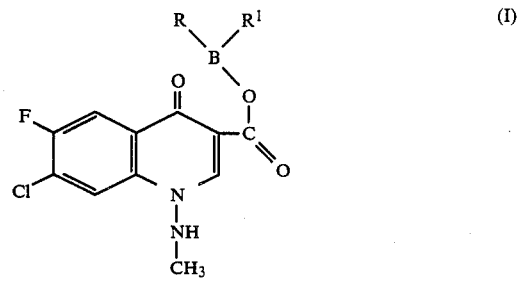

(wherein R and $R^1$ stand for halogen; an aliphatic acyloxy group comprising 2–6 carbon atoms and optionally substituted by halogen; or an aromatic acyloxy group comprising 7–11 carbon atoms).

The new compounds of the general Formula I are valuable intermediates useful in the preparation of the antibacterial agent 6-fluoro-1-methylamino-7-(4-methylpiperazino)-4-oxo-1,4-dihydro-quinoline-3- carboxylic acid.

The new compounds of the general Formula I may be prepared by reacting a compound of the Formula II

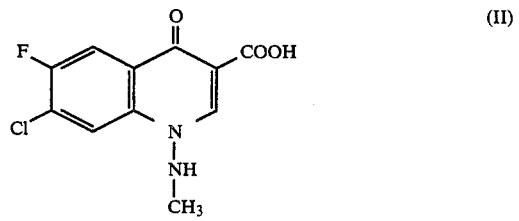

or a compound of the general Formula III

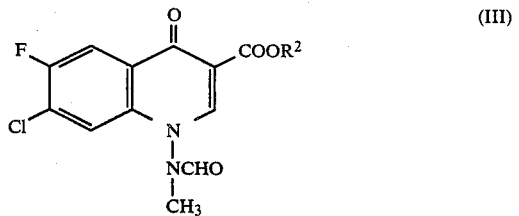

(wherein $R^2$ stands for alkyl comprising 1–4 carbon atoms) with hydrogen fluoro borate of the Formula IV

HBF₄    /IV/ or a borone trihalide of the general Formula V

BX₃    /V/

(wherein X stands for fluorine, chlorine or bromine) or a complex thereof formed with an ether or a borone derivative of the general Formula VI

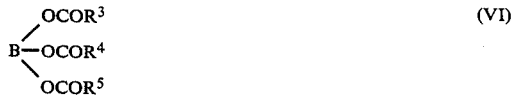

(wherein $R^3$, $R^4$ and $R^5$ stand for alkyl comprising 1–5 carbon atoms and optionally substituted by halogen or aryl comprising 6–10 carbon atoms).

6 Claims, No Drawings

BORIC ANHYDRIDES OF 6-FLUORO-7-CHLORO-1-METHYLAMINO-4-OXO-1,4-DIHYDRO-QUINOLINE-3-CARBOXYLIC ACID

This invention relates to new Amifloxacine intermediates and a process for the preparation thereof. More particularly it is concerned with new anhydrides of 6-fluoro-7-chloro-1-methylamino-4-oxo-1,4-dihydroquinoline-3-carboxylic acid and boric acids.

Ethyl-6-fluoro-7-chloro-1-methylamino-4-oxo-1,4-dihydro-quinoline-3-carboxylate is an intermediate useful in the preparation of the antibacterial agent 6-fluoro-1-methylamino-7-(4-methyl-piperazino)-4-oxo-1,4-dihydro-quinoline-3-carboxylic acid (Journal of Medicinal Chemistry, 27, 1103, (1984). The latter compound can be prepared in two steps from ethyl-6-fluoro-7-chloro-1-methylamino-4-oxo-1,4-dihydro-quinoline-3-carboxylate. The said ester is subjected to hydrolysis whereupon the 6-fluoro-7-chloro-1-methylamino-4-oxo-1,4-dihydro-quinoline-3-carboxylic acid thus obtained is reacted in the presence of a solvent at a temperature above 100° C. with 1-methyl-piperazine for 15–22 hours to yield the desired 6-fluoro-1-methylamino-7-(4-methylpiperazino)-4-oxo-1,4-dihydro-quinoline-3-carboxylic acid (European patent specification No. 90,424; Japanese patent specification No. 84 01,468).

It has been found that the 6-fluoro-1-methylamino-7-(4-methyl-piperazino)-4-oxo-1,4-dihydro-quinoline-3-carboxylic acid can be prepared under milder reaction conditions during a shorter reaction time by reacting 1-methyl-piperazine with a compound of the Formula I.

According to an aspect of the present invention there are provided new compounds of the Formula I

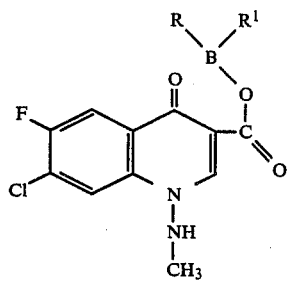

(wherein R and $R^1$ stand for halogen; an aliphatic acyloxy group comprising 2–6 carbon atoms and optionally substituted by halogen; or an aromatic acyloxy group comprising 7–11 carbon atoms).

According to a further aspect of the present invention there is provided a process for the preparation of the compounds of the Formula I (wherein R and $R^1$ stand for halogen; an aliphatic acyloxy group comprising 2–6 carbon atoms and optionally substituted by halogen; or an aromatic acyloxy group comprising 7–11 carbon atoms), which comprises (a) reacting the quinoline-3-carboxylic acid derivative of the Formula II

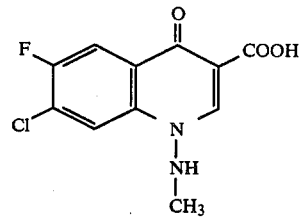

with fluoroboric acid of the Formula IV or a trihalo borate of the Formula V $$BX_3 \qquad (V)$$

(wherein X stands for fluorine, chlorine or bromine) or a triacyloxy borate derivative of the Formula VI

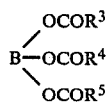

(wherein $R^3$, $R^4$ and $R^5$ stand for alkyl comprising 1–4 carbon atoms and optionally substituted by halogen; or aryl comprising 6–10 carbon atoms); or (b) reacting a quinoline derivative of the Formula III

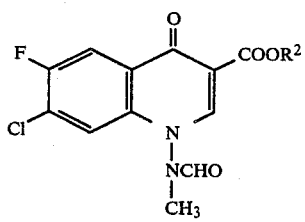

(wherein $R^2$ stands for hydrogen or alkyl comprising 1–4 carbon atoms) with fluoro boric acid of the Formula IV, or a trihalogeno borate of the Formula V (wherein X has the same meaning as stated above) or a triacyloxy borate of the Formula VI (wherein $R^3$, $R^4$ and $R^5$ are as stated above).

As compound of the Formula V borone trifluoride, boron tribromide or boron trichloride or a complex or aqueous solution thereof can be used. One may preferably use a complex formed with an ether or alcohol (e.g. a complex of boron trifluoride formed with tetrahydrofuran, diethyl ether, methanol, or propanol). One may preferably use a solution of a boron trihalide formed with an aliphatic hydrocarbon (e.g. dichloro methane) or a carboxylic acid (e.g. acetic acid, trifluoro acetic acid or propionic acid).

The boric acid of the Formula IV, the boron trihalide of the Formula V or the compound of the Formula VI can be used in a molar ratio of 1–50— preferably 1–5— related to 1 mole of the compound of the Formula II or III. The above molar ratio is however but a preferable feature and an other molar ratio may be applied as well.

The above reactions may be carried out, if desired, in the presence of a solvent. As solvent e.g. water, ketones (e.g. acetone, methyl-ethyl-ketone), hydrocarbons (e.g. hexane, benzene, toluene), ethers (e.g. diethyl ether, dioxane, tetrahydrofuran), organic acids (e.g. acetic acid, propionic acid, trifluoro acetic acid, etc.) may be used.

The reactions can be carried out at room temperature, if desired.

On raising the reaction temperature, the reaction time can be shortened. Some reactions can be accomplished at a temperature between room temperature and 150° C. The reaction temperature depends on the solvent used as well.

The compound of the Formula I thus obtained, precipitates from the reaction mixture spontaneously or on cooling and can be isolated by known methods (e.g. filtration).

Further details of the present invention are to be found in the following Examples without limiting the scope of protection to the said Examples.

EXAMPLE 1

5 g of ethyl-6-fluoro-1-(N-formyl-N-methyl-amino)-7-chloro-4-oxo-1,4-dihydro-quinoline-3-carboxylate are stirred in 25 ml of an 50 weight/vol % aqueous solution of hydrogen fluoroboric acid at 90°–95° C. for 4 hours. After one hour and a half the precipitation of crystals begins. The reaction mixture is cooled to room temperature, then placed into a refrigerator and allowed to crystallize overnight. The precipitated crystals are filtered next morning and washed with some water. Thus 4.55 g of an anhydride of 6-fluoro-7-chloro-1-(methylamino)-4-oxo-1,4-dihydro-quinoline-3-carboxylic acid and difluoro boric acid are obtained, yield: 93.4%. Mp.: 277° C. (decomposition).

Analysis for the Formula $C_{11}H_7BF_3ClN_2O_3$: calculated: C=41.48%, H=2.21%, N=8.79%; found: C=41.59%, H=2.34%, N=8.58%.

EXAMPLE 2

5 g of 6-fluoro-7-chloro-1-methylamino-4-oxo-1,4-dihydro-quinoline-3-carboxylic acid are stirred in 25 ml of a 50 weight/vol % aqueous solution of hydrogen fluoro boric acid at 80°–90° C. for 2 hours. After 45 minutes the precipitation of crystals begins. The reaction mixture is first cooled to room temperature and then allowed to crystallize for 2 hours at 0° C. The precipitated crystals are filtered, and washed with some water. Thus 4.95 g of an anhydride of 6-fluoro-7-chloro-1-methylamino-4-oxo-1,4-dihydro-quinoline-3-carboxylic acid and difluoro boric acid are obtained, yield 84.5%. Mp.: 277° C. (decomposition). A mixture of the product thus obtained with any amount of the compound prepared according to Example 1 shows no melting point depression.

EXAMPLE 3

A mixture of 1.42 g of boric acid and 10.7 g of propionic anhydride is stirred at 100° C. for 15 minutes whereupon the reaction mixture is heated to boiling point. After 30 minutes the temperature of the reaction mixture is lowered to 110° C. and 4.2 g of 6-fluoro-7-chloro-1-methylamino-4-oxo-1,4-dihydro-quinoline-3-carboxylic acid are added. After some minutes the precipitation of crystals begins. The reaction mixture is stirred at 110° C. for 2 hours, cooled to 10° C., whereupon 20 ml of water and 20 ml of ethanol are added to the crystalline suspension. The reaction mixture is allowed to crystallize in a refrigerator overnight. The precipitated crystals are filtered, washed with water and dried. Thus 6.12 g of (6-fluoro-7-chloro-1-methylamino-4-oxo-1,4-dihydro-quinoline-3-carboxylic acid-boron-dipropionyloxy)-anhydride are obtained. Yield: 93.5%, Mp.: 215° C. (decomposition).

Analysis for the Formula $C_{17}H_{17}BFClN_2O_7$: calculated: C=47.86%, H=4.01%, N=6.56%; found: C=48.07%, H=3.87%, N=6.48%.

EXAMPLE 4

0.568 g of boric acid and 3.28 g of acetic acid anhydride are reacted in the presence of 1 mg zinc chloride, while the temperature of the reaction raises to 40° C. The white suspension is slowly heated to 100° C. and 2 g ethyl [7-chloro-6-fluoro-1,4-dihydro-1-(formylmethyl-amino)-4-oxo-3-quinoline-carboxylate] are added which had previously been dissolved in 10 ml of 96% by W/V acetic acid. The reaction mixture is further heated at 110° C. for 2 hours. The solution is cooled to room temperature and diluted with 40 ml of cold water. The precipitated crystals are filtered and washed with water and cold abs. ethanol, and dried. Off-white crystalline [6-fluoro-7-chloro-1,4-dihydro-1-(methyl-amino)-4-oxo-3-quinolinecarboxylate-$O^3,O^4$]-bis(acetate-O)-boron is obtained (1.75 g).

Decomposition: 272° C.

Upon standing further 0.45 g product is precipitated from the mother-liquor.

Analysis for the formula $C_{15}H_{13}BClFN_2O_7$: calculated: C=45.55%, H=3.31%, N=3.54%; found: C=45.2%, H=3.2%, N=3.6%.

What we claim is:

1. A compound of the Formula I

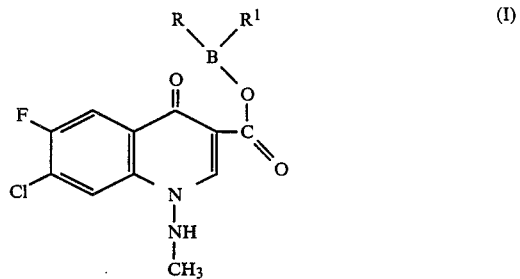

wherein R and $R^1$ stand for halogen; $C_2$ to $C_6$ alkanoyloxy or benzoyloxy.

2. The compound of the Formula (I) defined in claim 1 wherein R and $R^1$ are each bromine, chlorine or fluorine.

3. The compound of the Formula (I) defined in claim 1 wherein R and $R^1$ are each acetoxy or propionyloxy.

4. A process for preparing a compound of the Formula (I)

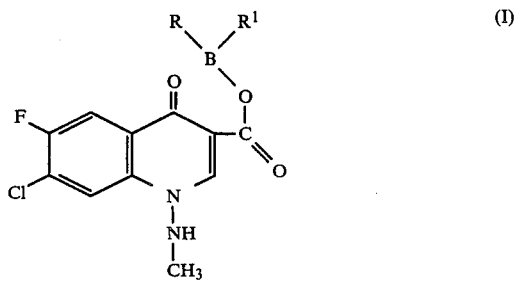

wherein R and R¹ are each bromine, chlorine or fluorine, which comprises halogenating a compound of the Formula (II)

*[Structure of Formula (II): 6-fluoro-7-chloro-4-oxo-1-(N-methylamino)-1,4-dihydroquinoline-3-carboxylic acid]* or a compound of the Formula (III)

*[Structure of Formula (III): 6-fluoro-7-chloro-4-oxo-1-(N-methyl-N-formylamino)-1,4-dihydroquinoline-3-carboxylic acid ester COOR²]* wherein $R^2$ is $C_1$ to $C_4$ alkyl (a) with hydrogen fluoro borate of the formula (IV)

$$HBF_4$$

to yield the compound of the Formula (I) where R and R¹ are each fluorine; or (b) with a boron trihalide of the Formula (V)

$$BX_3$$

where X is bromine, chlorine or fluorine, or a complex thereof formed with an ether or an alcohol, to yield the compound of the Formula (I) where R and R¹ are each bromine, chlorine or fluorine.

5. The process according to claim 4 which comprises carrying out the reaction of the compound of the Formula II or III with the compound of the Formula IV in aqueous medium.

6. The process according to claim 4 which comprises reacting the compound of the Formula II or III with the compound of the Formula V in the presence of a solvent.

* * * * *

UNITED STATES PATENT AND TRADEMARK OFFICE
CERTIFICATE OF CORRECTION

PATENT NO. : 4,806,645

DATED : 21 February 1989

INVENTOR(S) : Istvan HERMECZ et al

It is certified that error appears in the above-identified patent and that said Letters Patent is hereby corrected as shown below: Title page:

Item [75] Inventors' names are to read:

Second name of the fourth inventor is to read:
-- Horvath --;

First name of the fifth inventor is to read:
-- Maria --;

First and second names of the sixth inventor is to read:
-- Gabor Kovacs --;

First name of the seventh inventor is to read:
-- Zoltan --;

First name of the ninth inventor is to read:
-- Peter --.

Signed and Sealed this

Thirty-first Day of October, 1989

*Attest:*

DONALD J. QUIGG

*Attesting Officer*  *Commissioner of Patents and Trademarks*